United States Patent [19]

Grove, deceased

[11] 4,400,530

[45] Aug. 23, 1983

[54] PROCESS FOR PREPARING SUBSTITUTED DIPHENYL ETHERS

[75] Inventor: William S. Grove, deceased, late of Doylestown, Ohio, by Louise A. Grove, administratrix

[73] Assignee: PPG Industries, Inc., Pittsburgh, Pa.

[21] Appl. No.: 243,002

[22] Filed: Mar. 12, 1981

Related U.S. Application Data

[63] Continuation-in-part of Ser. No. 163,460, Jun. 27, 1980, which is a continuation-in-part of Ser. No. 65,480, Jul. 25, 1979.

[51] Int. Cl.$^3$ ............................................. C07C 79/46
[52] U.S. Cl. .............................. 560/21; 260/455 R; 260/465 D
[58] Field of Search .......... 560/21; 260/455 R, 465 D

[56] References Cited

U.S. PATENT DOCUMENTS 3,928,416 12/1975 Bayer et al. ........................... 560/21

FOREIGN PATENT DOCUMENTS 20052 10/1980 European Pat. Off. .............. 560/21

*Primary Examiner*—Paul J. Killos
*Attorney, Agent, or Firm*—Edward J. Whitfield; Irwin M. Stein; Linda Pingitore

[57] ABSTRACT

A process for preparing a diphenyl ether of the formula:

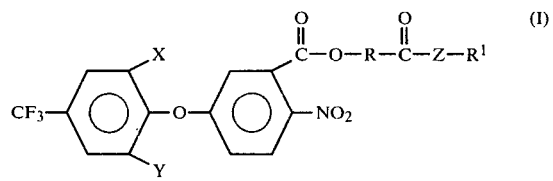

wherein:
X is hydrogen or halogen;
Y is hydrogen, halogen, cyano, trifluoromethyl, or an alkyl radical containing 1 to 4 carbon atoms;
Z is oxygen or sulfur;
R is a methylidene or monosubstituted methylidene, wherein the substituent is selected from the group consisting of alkyl, oxoalkyl and hydroxyalkyl radicals containing from 1 to 4 carbon atoms; and
R$^1$ is hydrogen, or an alkyl radical containing from 1 to 8 carbon atoms, a cycloalkyl radical containing from 3 to 8 carbon atoms, an agronomically acceptable cationic salt, phenyl, or mono-, di-, or trisubstituted phenyl, said substituents being selected from the group consisting of halogen, alkyl or alkoxy radicals containing from 1 to 10 carbon atoms, cyano, nitro, and trifluoromethyl;

which comprises the sequential steps of:
(a) reacting a diphenyl ether of the formula:

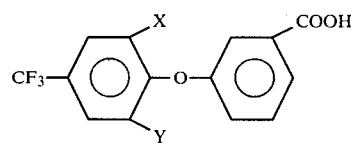

wherein X and Y are as defined, with an inorganic alkali metal base to form the corresponding acid salt;
(b) reacting the acid salt of step (a) with an α-halocarboxylic acid ester of the formula:

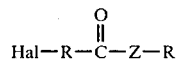

wherein R and Z are as defined; R$^1$ is an alkyl radical containing from 1 to 8 carbon atoms, a cycloalkyl radical containing from 3 to 8 carbon atoms, an agronomically acceptable cationic salt, phenyl, or mono-, di-, or trisubstituted phenyl, said substituents being selected from the group consisting of halogen, alkyl or alkoxy radicals containing from 1 to 10 carbon atoms, cyano, nitro, and trifluoromethyl; and Hal is selected from the group consisting of chlorine, bromine and iodine, to form the corresponding ester; and
(c) nitrating the ester product of step (b).

14 Claims, No Drawings

PROCESS FOR PREPARING SUBSTITUTED DIPHENYL ETHERS

CROSS REFERENCE TO THE RELATED APPLICATIONS

This application is a continuation-in-part of my copending application Ser. No. 163,460, filed, June 27, 1980, which application is a continuation-in-part of my copending application Ser. No. 65,480, filed July 25, 1979.

DESCRIPTION OF THE INVENTION

This invention relates to a process for the preparation of certain substituted diphenyl ethers having herbicidal activity. More particularly, this invention concerns a sequence of reaction steps for preparing substituted diphenyl ethers which are represented by the graphic formula:

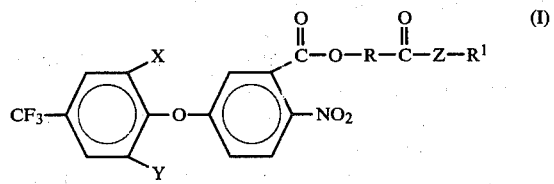

wherein:
X is hydrogen or halogen;
Y is hydrogen, halogen, cyano, trifluoromethyl, or an alkyl radical containing 1 to 4 carbon atoms;
Z is oxygen or sulfur;
R is a methylidene or monosubstituted methylidene, wherein the substituent is selected from the group consisting of alkyl, oxoalkyl and hydroxyalkyl radicals containing from 1 to 4 carbon atoms; and
$R^1$ is hydrogen, or an alkyl radical containing from 1 to 8 carbon atoms, a cycloalkyl radical containing from 3 to 8 carbon atoms, an agronomically acceptable cationic salt, phenyl, or mono-, di-, or trisubstituted phenyl, said substituents being selected from the group consisting of halogen, alkyl or alkoxy radicals containing from 1 to 10 carbon atoms, cyano, nitro, and trifluoromethyl.

Exemplary of halogens represented in the above formula are bromine, chlorine, iodine, or fluorine, preferably bromine or chlorine. Representative examples of alkyl and cycloalkyl groups represented in the above formula include: methyl, ethyl, isobutyl, n-butyl, t-butyl, n-amyl, heptyl, octyl, iso-octyl, nonyl, decyl, cyclopropyl, cyclopentyl, cyclohexyl, cyclooctyl, and the like. Suitable alkoxy, oxoalkyl and hydroxyalkyl groups are, for example, methoxy, ethoxy, butoxy, octoxy, oxoethyl, oxopropyl, oxobutyl, hydroxymethyl, hydroxyethyl, hydroxypropyl, hydroxybutyl, and the like. As examples of agronomically acceptable cationic salts, there may be mentioned alkali metals such as sodium, potassium, or lithium; alkaline earth metals such as barium, magnesium, or calcium; ammonium; or alkylammonium and alkanolammonium containing 1 to 4 carbon atoms.

Preferred diphenyl ether compounds of this invention are those wherein Z is oxygen, $R^1$ is alkyl of up to 4 carbon atoms, X is hydrogen, and Y is halogen. Some specific examples of compounds within the scope of Formula I are: 1'-(ethoxycarbonyl)ethyl 5-(2-chloro-4-trifluoromethylphenoxy)-2-nitrobenzoate; 2'-ethoxycarbonyl 5-(2-chloro-4-trifluoromethylphenoxy)-2-nitrobenzoate; 1'-(ethoxycarbonyl)methyl 5-(2-chloro-4-trifluoromethylphenoxy)-2-nitrobenzoate; 1'-ethoxycarbonyl-2-oxopropyl-5-(2-chloro-4-trifluoromethylphenoxy)-2-nitrobenzoate; 1'-(ethoxycarbonyl)-butyl 5-(2-chloro-4-trifluoromethylphenoxy)-2-nitrobenzoate; 1'-(phenoxycarbonyl)ethyl 5-(2-chloro-4-trifluoromethylphenoxy)-2-nitrobenzoate; 1'-(ethoxycarbonyl)propyl 5-(2-chloro-4-trifluoromethylphenoxy)-2-nitrobenzoate; 1'-ethoxycarbonyl-3'-methylbutyl 5-(2-chloro-4-trifluoromethylphenoxy)-2-nitrobenzoate; 1'-(ethoxycarbonyl)ethyl 5-(2,6-dichloro-4-trifluoromethylphenoxy)-2-nitrobenzoate; and 1'-(thioethylcarbonyl)ethyl 5-(2-chloro-4-trifluoromethylphenoxy)-2-nitrobenzoate.

In accordance with the present invention, diphenyl ethers represented by Formula I are prepared by the sequential steps of:

(a) reacting a diphenyl ether of the formula:

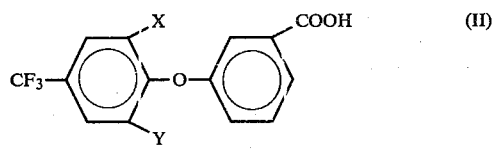

wherein X and Y are as defined with respect to Formula I with an inorganic alkali metal base to form the corresponding acid salt;

(b) reacting said acid salt with an α-halocarboxylic acid ester to form the corresponding ester; and (c) nitrating the ester product of step (b) to form a diphenyl ether of Formula I.

In Formula II, X is preferably halogen. Of the halogens, X is more preferably chlorine. Y is preferably hydrogen.

Any moderately strong to strong inorganic alkali metal base can be used to generate the acid salt of step (a). Suitable bases include alkali metal hydroxides such as potassium hydroxide, sodium hydroxide and lithium hydroxide; sodium carbonate; potassium carbonate, or the like. In a preferred embodiment, potassium hydroxide is utilized.

The acid salt is generally prepared in a polar organic solvent, such as $C_1$–$C_4$ saturated aliphatic alcohol, dimethylsulfoxide, or N, N-dimethylformamide, at temperatures from about 50° C. to 200° C. Preferably a $C_1$–$C_4$ aliphatic alcohol, e.g., methanol, ethanol, propanol, or butanol, is utilized. Of these, methanol is more preferably utilized. When the solvent is an alcohol such as methanol, the solvent is removed and the acid salt isolated, for instance, by distillation, prior to esterification with the α-halocarboxylic acid ester. The acid salt can also be prepared using aqueous base, e.g., 50 weight percent KOH. In that case, the salt is isolated usually by adding polar aprotic solvent together with an organic solvent such as toluene. If desired, some or all of the water can be removed by distillation as an azeotrope, i.e., a mixture of two or more compounds with constant boiling points resulting in a distillate having the same composition as the original mixture.

The α-halocarboxylic acid ester utilized in the second step of the above-described process can be represented by the graphic formula:

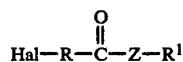
(III)

wherein R and Z are as defined with respect to Formula I; $R^1$ is an alkyl radical containing from 1 to 8 carbon atoms, a cycloalkyl radical containing from 3 to 8 carbon atoms, phenyl, or mono, di-, or trisubstituted phenyl, said substituents being selected from the group consisting of halogen, alkyl or alkoxy radicals containing from 1 to 10 carbon atoms, cyano, nitro, and trifluoromethyl; and Hal is selected from chlorine, bromine and iodine. In a preferred embodiment, R is methyl substituted methylidene, $R^1$ is ethyl, Z is oxygen, and Hal is chlorine, i.e., ethyl 2-chloropropionate. Moreover, the various sterioisomeric forms of the aforesaid esterifying agent can be utilized. The esterification is generally performed in the liquid phase at temperatures from about 50° C. to 200° C., preferably 90° C. to 140° C., using equimolar amounts of the acid salt and α-halocarboxylic acid ester. An excess amount of acid salt may also be utilized. A 1 to 5 weight percent excess of the α-halocarboxylic acid ester may be advantageous in helping to insure completion of the reaction. The reaction generally is performed in a polar aprotic organic solvent such a dimethylsulfoxide, N,N-dimethylformamide, sulfolane, N-methyl-2-pyrrolidone, hexamethylphosphoric diamide, or mixtures of such solvents. In a preferred embodiment, dimethylsulfoxide is utilized.

The mixture of acid salt, α-halocarboxylic acid ester and organic solvent is heated to the desired temperature and maintained at that temperature until the reaction attains the desired extent of completion. A sample of the reaction mixture can be analyzed by thin layer chromatography (TLC) to determine the extent of completion of the esterification. The reaction mixture is then cooled to ambient temperature, washed with water and allowed to phase separate. The α-halocarboxylic acid ester-substituted diphenyl ether product is recovered from the organic phase by any known method such as for example, evaporation, cystallization, or vacuum drying.

The final reaction step in the above-described process comprises nitrating the ester product of step (b) with a nitrating agent. The nitration is typically carried out at temperatures from about 0° C. to 70° C., more preferably 20° C. to 50° C. In a preferred embodiment of this invention, the nitration is conducted under a nitrogen atmosphere in order to maintain a substantially anhydrous reaction medium. Any conventional nitrating agent can be utilized. Preferred nitrating agents include nitric acid, mixed acids such as nitric acid/sulfuric acid, potassium nitrate/sulfuric acid, or nitric acid/sulfuric acid/acetic anhydride. More preferably, a nitric acid/sulfuric acid/acetic anhydride mixture is utilized. Generally, from a stoichiometric amount to an excess of nitrating agent is utilized although typically an excess amount is utilized. More usually, a 10 to 50 percent molar excess of nitrating agent to diphenyl ether reactant is utilized, preferably a 40 percent excess.

An inert organic solvent, that is a solvent inert to the reactants as well as the product of the reaction, can also be used. Exemplary of inert organic solvents are $C_5$–$C_{12}$ aliphatic hydrocarbons; $C_5$–$C_7$ cyclic aliphatic hydrocarbons; $C_5$–$C_7$ cyclic aliphatic hydrocarbons; $C_1$–$C_6$ halogenated aliphatic hydrocarbons; $C_6$–$C_{10}$ aromatic hydrocarbons; and $C_6$–$C_{10}$ halogenated aromatic hydrocarbons. Some examples of suitable solvents are diethyl ether, cyclohexane, hexane, heptane, methylene chloride, methylene dichloride, ethylene dichloride, chloroform, perchloroethylene, benzene, toluene, monochlorobenzene, and dichlorobenzene.

After the nitration reaction is complete, the reaction mixture is phase separated, washed with water, and topped under vacuum to afford the substituted diphenyl ether product of Formula I. Typically, a product of substantial purity, which is determined by TLC, is obtained.

The process of the present invention can be conducted batchwise or continuously. A continuous process for the preparation of a substituted diphenyl ether of Formula I comprises the continuous steps, in sequence, of:

(a) reacting a diphenyl ether of Formula II with an inorganic alkali metal base to form an acid salt;

(b) esterifying the acid salt of step (a) with an α-halocarboxylic acid ester of Formula III; and (c) nitrating the ester product of step (b), withdrawing a portion of the reaction medium containing substituted diphenyl ether product and introducing additional reactants to maintain the desired quantity in the reaction medium.

In accordance with the present invention, a diphenyl ether of Formula I, for example, 1'-(ethoxycarbonyl) ethyl 5-(2-chloro-4-trifluoromethylphenoxy)-2-nitrobenzoate, can be prepared by the sequential steps of (a) acid salt formation, (b) esterification, and (c) nitration.

The acid salt of step (a), for example, a potassium salt, is formed by reacting a diphenyl ether of Formula II, e.g., 5-(2-chloro-4-trifluoromethylphenoxy)benzoic acid, with an inorganic alkali metal base, in this case, potassium hydroxide, in the presence of a polar organic solvent such as methanol, at temperatures from about 50° C. to 200° C. The solvent and water are removed by distillation and the aforesaid acid salt is esterified with an α-halocarboxylic acid ester, e.g., ethyl 2-chloropropionate, in the presence of a polar aprotic organic solvent, such as dimethylsulfoxide at temperatures from about 50° C. to 200° C. The reaction mixture is heated to and maintained at its reflux temperature until the reaction is completed, whereupon it is cooled to ambient temperature, washed with water, and allowed to phase separate. The ethyl 2-chloropropyl ester-substituted diphenyl ether is recovered, for example, by vacuum drying.

In the final reaction step, the aforesaid ester-substituted diphenyl ether is nitrated under a nitrogen atmosphere with a nitrating agent such as a nitric acid/sulfuric acid/acetic anhydride mixture, in the presence of an inert organic solvent such as methylene chloride at temperatures from about 0° C. to 70° C. The reaction mixture is phase separated, washed with water, topped under vacuum and the diphenyl ether product recovered by crystallization.

The present invention is more particularly described in the following Examples which are intended as being illustrative only since numerous modifications and variations therein will be apparent to those skilled in the art.

EXAMPLE I

Esterification of 5-(2-chloro-4-trifluoromethylphenoxy)benzoic acid with ethyl 2-chloropropionate Into a one-liter, three-necked flask equipped with a thermometer, condenser, and a power-driven stirring device was placed 0.525 mole (29.4 grams) anhydrous potassium hydroxide in 350 milliliters of methanol. After dissolution of the potassium hydroxide, the mixture was cooled to 50° C. and 0.5 mole (157.7 grams) of 5-(2-chloro-4-trifluoromethylphenoxy)benzoic acid in 250 milliliters of methanol was added. The flask was then equipped for distillation and two-thirds of the methanol (approximately 530 milliliters) was distilled off. Toluene (150 milliliters) was added and distillation continued until all the water was removed azeotropically.

The reaction mixture was then cooled to 50° C. Subsequently, 200 milliliters of dimethylsulfoxide and 0.5 mole (68.25 grams) of ethyl 2-chloropropionate were added followed by heating of the reaction mixture to 110° C. for 16 hours.

The reaction mixture was allowed to cool and then poured into 500 milliliters of water. Methylene chloride (200 milliliters) was added and the layers separated. The organic layer was washed with five 250 milliliter portions of water, dried over magnesium sulfate, and stripped on a rotovac. A 79.2 percent yield of product was obtained according to High Pressure Liquid Chromatographic (HPLC) analysis.

EXAMPLE II

Nitration of 1'(ethoxycarbonyl)ethyl (2-chloro-4-trifluoromethylphenoxy)benzoate Into a 500-milliliter four-necked flask equipped with thermometer, condenser, power-driven propelling device, and nitrogen atmosphere, was placed 2.71 moles (1130 grams) of 1'-(ethoxycarbonyl)ethyl (2-chloro-4-trifluoromethylphenoxy)benzoate, 1500 ml of methylene chloride, 8.13 moles (768 ml) of acetic anhydride, and 851 ml of concentrated sulfuric acid.

To the aforesaid reaction mixture were added, dropwise, 2.71 moles (174 ml) of concentrated nitric acid over a one-hour period at 20°-25° C. Subsequently, an additional 3.25 moles (307 ml) of acetic anhydride and 1.08 moles (70 ml) of nitric acid were added over a 30-minute period. The reaction mixture was stirred at ambient temperature overnight. The progress of the reaction was monitored at selected intervals by thin layer chromatographic analysis (TLC) of aliquots of the reaction mixture.

The reaction mixture was then poured into 15 liters of water and phase separated. The organic phase was washed with 2 liters of 4% aqueous sodium hydroxide and 2 liters of 6% aqueous ammonia. (Saturated sodium chloride solution was added to assist phase separation). The organic phase was washed again with 100 milliliters of water, phase separated, dried with magnesium sulfate, filtered, and topped in vacuum to 75° C.

The thick liquid 1'-(ethoxycarbonyl)ethyl (2-chloro-4-trifluoromethylphenoxy)-2-nitro-5-benzoate, product weighed 1115 grams. TLC analysis of this product material revealed it to be substantially pure; which result was confirmed by a High Pressure Liquid Chromatographic (HPLC) analysis of 75%.

While the invention has been described with reference to specific details of certain illustrative embodiments, it is not intended that it should be limited thereby, except insofar as such details appear in the accompanying claims.

I claim:

1. A process for preparing a diphenyl ether of the graphic formula:

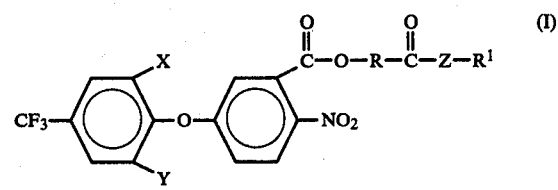

wherein:
X is hydrogen or halogen;
Y is hydrogen, halogen, cyano, trifluoromethyl, or an alkyl radical containing from 1 to 4 carbon atoms;
Z is oxygen or sulfur;
R is a methylidene or monosubstituted methylidene, wherein the substituent is selected from the group consisting of alkyl, oxoalkyl and hydroxyalkyl radicals containing from 1 to 4 carbon atoms; and
$R^1$ is hydrogen, or an alkyl radical containing from 1 to 8 carbon atoms, a cycloalkyl radical containing from 3 to 8 carbon atoms, an agronomically acceptable cationic salt, phenyl, or mono-, di-, or trisubstituted phenyl, said substituents being selected from the group consisting of halogen, alkyl or alkoxy radicals containing from 1 to 10 carbon atoms, cyano, nitro, and trifluoromethyl;
which comprises the sequential steps of:
(a) reacting a diphenyl ether of the graphic formula:

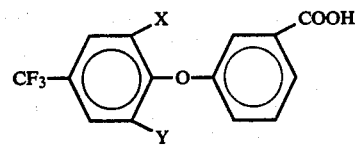

wherein X and Y are as defined above, with an inorganic alkali metal base to form the corresponding acid salt;
(b) reacting the acid salt of step (a) with an α-halocarboxylic acid ester of the graphic formula:

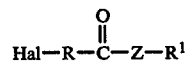

wherein R and Z are as defined above; $R^1$ is an alkyl radical containing from 1 to 8 carbon atoms, a cycloalkyl radical containing from 3 to 8 carbon atoms, phenyl, or mono-, di-, or trisubstituted phenyl, said substituents being selected from the group consisting of halogen, alkyl or alkoxy radicals containing from 1 to 10 carbon atoms, cyano, nitro, and trifluoromethyl; and Hal is selected from the group consisting of chlorine, bromine and iodine, to form the corresponding ester; and
(c) nitrating the ester product of step (b) with a nitrating agent selected from the group consisting of nitric acid; mixtures of nitric acid and sulfuric acid; mixtures of potassium nitrate and sulfuric acid; and mixtures of nitric acid, sulfuric acid, and acetic anhydride, thereby to form a diphenyl ether represented by graphic Formula I.

2. The process of claim 1 wherein the diphenyl ether of Formula I is 1′(ethoxycarbonyl)ethyl 5-(2-chloro-4-trifluoromethylphenoxy)-2-nitrobenzoate.

3. The process of claim 1 wherein ethyl-2-chloropropionate is the α-halocarboxylic acid ester.

4. The process of claim 1 wherein the inorganic alkali metal base is an alkali metal hydroxide.

5. The process of claim 4 wherein the nitrating agent is a mixture of nitric acid, sulfuric acid and acetic anhydride.

6. A process for preparing a diphenyl ether of the graphic formula:

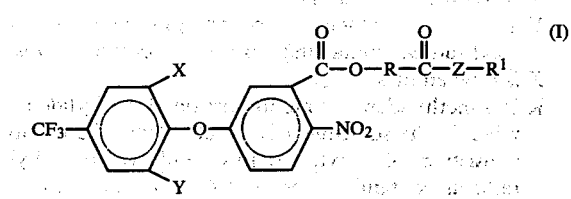

wherein:
X is hydrogen or halogen;
Y is hydrogen, halogen, cyano, trifluoromethyl, or an alkyl radical containing from 1 to 4 carbon atoms;
Z is oxygen or sulfur;
R is methylidene or monosubstituted methylidene, wherein the substituent is selected from the group consisting of alkyl, oxoalkyl and hydroxyalkyl radicals containing from 1 to 4 carbon atoms; and
$R^1$ is hydrogen, or an alkyl radical containing from 1 to 8 carbon atoms, a cycloalkyl radical containing from 3 to 8 carbon atoms, an agronomically acceptable cationic salt, phenyl, or mono-, di-, or trisubstituted phenyl, said substituents being selected from the group consisting of halogen, alkyl or alkoxy radicals containing from 1 to 10 carbon atoms, cyano, nitro, and trifluoromethyl;

which comprises the sequential steps of:
(a) reacting a diphenyl ether of the graphic formula:

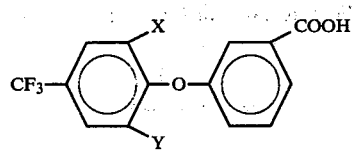

wherein X and Y are as defined above, with potassium hydroxide in the presence of methanol at temperatures from about 50° C. to 200° C. to form the corresponding acid salt;
(b) reacting the acid salt of step (a) with ethyl-2-chloropropionate in the presence of dimethylsulfoxide at temperatures from about 50° C. to 200° C. to form the corresponding ester; and
(c) nitrating the ester product of step (b) with a mixture of nitric acid, sulfuric acid and acetic anhydride as nitrating agent.

7. The process of claim 6 wherein the esterification reaction is performed at temperatures from 90° C. to 140° C.

8. The process of claim 6 wherein a 1 to 5 weight percent excess of ethyl-2-chloropropionate is utilized.

9. The process of claim 6 wherein the nitration reaction is performed at temperatures from about 0° C. to 70° C.

10. The process of claim 9 wherein the nitration reaction is performed at temperatures from about 20° C. to 50° C.

11. The process of claim 6 wherein a 10 to 50 percent molar excess of nitrating agent is utilized.

12. The process of claim 11 wherein a 40 percent molar excess is utilized.

13. The process of claim 6 wherein the nitration reaction is conducted under a nitrogen atmosphere.

14. A process for the continuous preparation of diphenyl ether of the formula:

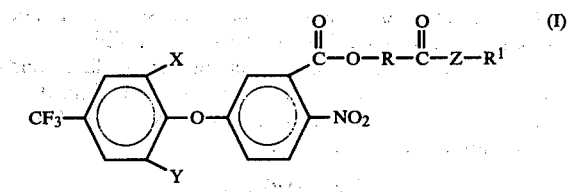

wherein:
X is hydrogen or halogen;
Y is hydrogen, halogen, cyano, trifluoromethyl, or an alkyl radical containing from 1 to 4 carbon atoms;
X is oxygen or sulfur;
R is a methylidene or monosubstituted methylidene, wherein the substituent is selected from the group consisting of alkyl, oxoalkyl and hydroxyalkyl radicals containing from 1 to 4 carbon atoms; and
$R^1$ is hydrogen, or an alkyl radical containing from 1 to 8 carbon atoms, a cycloalkyl radical containing from 3 to 8 carbon atoms, an agronomically acceptable cationic salt, phenyl, or mono-, di-, or trisubstituted phenyl, said substituents being selected from the group consisting of halogen, alkyl or alkoxy radicals containing from 1 to 10 carbon atoms, cyano, nitro, and trifluoromethyl;

which comprises the sequential steps of:
(a) reacting a diphenyl ester of Formula II with an inorganic alkali metal base to form an acid salt;
(b) esterifying the acid salt of step (a) with an halocarboxylic acid ester of Formula III; and
(c) nitrating the ester product of step (b), withdrawing a portion of reaction medium containing diphenyl ether product and introducing additional reactants to maintain the desired quantity in the reaction medium.

* * * * *